United States Patent
Seo et al.

(10) Patent No.: US 12,002,207 B2
(45) Date of Patent: Jun. 4, 2024

(54) DEVICE AND METHOD FOR CONSTRUCTING BLOOD VESSEL MAP, AND COMPUTER PROGRAM FOR EXECUTING SAID METHOD

(71) Applicants: SAMSUNG LIFE PUBLIC WELFARE FOUNDATION, Seoul (KR); KOREA UNIVERSITY RESEARCH AND BUSINESS FOUNDATION, Seoul (KR)

(72) Inventors: Woo-Keun Seo, Seoul (KR); Ji-Eun Lee, Seoul (KR); Ha-Na Song, Seoul (KR); In-Young Baek, Seoul (KR); Jun Kyung Seong, Seoul (KR); Hye Ryun Kim, Seoul (KR)

(73) Assignees: SAMSUNG LIFE PUBLIC WELFARE FOUNDATION, Seoul (KR); KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 565 days.

(21) Appl. No.: 17/297,264

(22) PCT Filed: Nov. 6, 2019

(86) PCT No.: PCT/KR2019/014967
§ 371 (c)(1),
(2) Date: May 26, 2021

(87) PCT Pub. No.: WO2020/111557
PCT Pub. Date: Jun. 4, 2020

(65) Prior Publication Data
US 2022/0028077 A1  Jan. 27, 2022

(30) Foreign Application Priority Data
Nov. 26, 2018 (KR) .................... 10-2018-0147687

(51) Int. Cl.
*G06T 7/00* (2017.01)
*G06T 7/30* (2017.01)

(52) U.S. Cl.
CPC ............ *G06T 7/0014* (2013.01); *G06T 7/30* (2017.01); *G06T 2207/10088* (2013.01); *G06T 2207/30101* (2013.01); *G06T 2207/30172* (2013.01)

(58) Field of Classification Search
CPC ............... G06T 7/0014; G06T 7/30; G06T 2207/10088; G06T 2207/30101;
(Continued)

(56) References Cited

U.S. PATENT DOCUMENTS 7,834,625 B2  11/2010 Doyle et al.
7,953,262 B2   5/2011 Suryanarayanan et al.
(Continued)

FOREIGN PATENT DOCUMENTS

JP   2017-91313 A   5/2017
KR  10-2008-0073238 A   8/2008
(Continued)

OTHER PUBLICATIONS

International Search Report dated Feb. 19, 2020 in International Application No. PCT/KR2019/014967 filed on Nov. 6, 2019, 2 pages.
(Continued)

*Primary Examiner* — Juan A Torres
(74) *Attorney, Agent, or Firm* — Oblon, McClelland, Maier & Neustadt, L.L.P.

(57) ABSTRACT

Disclosed herein a method of constructing a blood vessel map, the method including: receiving, by a blood vessel map construction apparatus, a TOF image of the object; extracting, by the blood vessel map construction apparatus, a blood vessel stem, a center line of a blood vessel, and features of the center line included in the TOF image, and detecting branch points of the blood vessel based on the extracted blood vessel stem, center line of the blood vessel, and
(Continued)

features of the center line; searching, by the blood vessel map construction apparatus, a reference blood vessel image corresponding to the TOF image in consideration of location information or curvature information of the branch points; calculating a similarity between the TOF image and the reference blood vessel image; and registering the TOF image in the blood vessel map based on the similarity.

9 Claims, 11 Drawing Sheets

(58) Field of Classification Search
CPC . G06T 2207/30172; G06T 2207/10081; G06T 2207/10116; G06T 2207/10132; G06T 7/0016; G06T 7/11; G06T 7/33; A61B 5/00; A61B 5/055; A61B 5/0036; A61B 5/004; G16H 30/20; G16H 30/40
USPC .......................................................... 382/128
See application file for complete search history.

(56) References Cited

U.S. PATENT DOCUMENTS

| 10,624,597 | B2 | 4/2020 | Nam et al. | |
|---|---|---|---|---|
| 2008/0188962 | A1* | 8/2008 | Suryanarayanan | .. G06V 10/457 |
| | | | | 700/89 |
| 2009/0086894 | A1* | 4/2009 | Boyden | ................ G01N 23/223 |
| | | | | 378/165 |
| 2012/0177275 | A1* | 7/2012 | Suri | ..................... A61B 8/0891 |
| | | | | 382/131 |
| 2013/0272596 | A1* | 10/2013 | Xu | ........................ G06V 10/426 |
| | | | | 382/134 |
| 2015/0055846 | A1* | 2/2015 | Haque | .................. A61B 5/7425 |
| | | | | 382/131 |
| 2015/0248757 | A1* | 9/2015 | Ohishi | .................... G06T 5/002 |
| | | | | 382/131 |
| 2019/0066296 | A1* | 2/2019 | Lee | ........................ A61B 8/0858 |
| 2022/0028077 | A1* | 1/2022 | Seo | ........................... G06T 7/30 |

FOREIGN PATENT DOCUMENTS

| KR | 10-2009-0075644 A | 7/2009 |
|---|---|---|
| KR | 10-1625955 B1 | 6/2016 |
| KR | 10-1635409 B1 | 7/2016 |
| KR | 10-2016-0103482 A | 9/2016 |
| WO | WO 2017/047819 A1 | 3/2017 |

OTHER PUBLICATIONS

Korean Office Action dated Mar. 19, 2021 in Korean Application No. 10-2018-0147687 filed on Nov. 26, 2018, (with unedited machine translation), 10 pages.

* cited by examiner

DEVICE AND METHOD FOR CONSTRUCTING BLOOD VESSEL MAP, AND COMPUTER PROGRAM FOR EXECUTING SAID METHOD

TECHNICAL FIELD

The present disclosure relates to an apparatus for constructing a blood vessel map, a method thereof, and a computer program for executing the method.

BACKGROUND ART

A magnetic resonance imaging (MRI) imaging device is a device that uses a magnetic field to image an object, and is widely used for accurate disease diagnosis because it three-dimensionally shows not only bones, but also discs, joints, nerve ligaments, heart, and cerebral blood vessels from a desired angle. Magnetic resonance imaging has the advantage of obtaining various contrast ratios by adjusting various parameters, and in clinical diagnosis, images of different contrast ratios are obtained for the same region using the contrast ratio, and diagnosis is performed. Korean Patent Publication No. 2009-0075644 discloses a magnetic resonance imaging apparatus that obtains a steady-state image of a patient by changing the spin phases of the patient's fat and water in order to generate a contrast ratio of the magnetic resonance image.

DESCRIPTION OF EMBODIMENTS

Technical Problem

One or more embodiments relate to an apparatus and method for constructing a blood vessel map that may obtain an average blood vessel image based on the age and region of Koreans, and a computer program for executing the method.

Solution to Problem

A method of constructing a blood vessel map according to embodiments of the present invention may include: receiving, by a blood vessel map construction apparatus, a TOF image of the object; extracting, by the blood vessel map construction apparatus, a blood vessel stem, a center line of a blood vessel, and features of the center line included in the TOF image, and detecting branch points of the blood vessel based on the extracted blood vessel stem, center line of the blood vessel, and features of the center line; searching, by the blood vessel map construction apparatus, a reference blood vessel image corresponding to the TOF image in consideration of location information or curvature information of the branch points; calculating a similarity between the TOF image and the reference blood vessel image; and registering the TOF image in the blood vessel map based on the similarity.

The extracting of the blood vessel stem, the center line of the blood vessel, and the features of the center line may include detecting a blood vessel region included in the TOF image, extracting a center line connecting voxels located at the center of the blood vessel from among voxels in the blood vessel by using a distance between voxels included in the blood vessel region and a boundary line of the blood vessel and a geodesic distance between the voxels, and obtaining information about the blood vessel stems and the branch points distributed in the blood vessels.

According to the present embodiment, after the searching of the reference blood vessel image, the TOF image is matched with the reference blood vessel image in consideration of centerlines of a blood vessel included in the TOF image and the reference blood vessel image.

The calculating of the similarity may include calculating a similarity between the blood vessel center line of the TOF image and a blood vessel center line of the reference blood vessel image and a correspondence relationship between the similarities, by calculating a similarity between the point of the TOF image and the point of the reference blood vessel image, and repeatedly calculating the similarity between the points.

A blood vessel map construction apparatus according to embodiments of the present invention may include an image input unit configure to receive a TOF image of the object; a preprocessor configured to extract a blood vessel stem, a center line of a blood vessel, and features of the center line included in the TOF image, and detect branch points of the blood vessel based on the extracted blood vessel stem, center line of the blood vessel, and features of the center line; a matching unit configure to search for a reference blood vessel image corresponding to the TOF image in consideration of location information or curvature information of branch points; a similarity calculator configured to calculate a similarity between the TOF image and the reference blood vessel image; and a data registration unit configured to register the TOF image in a blood vessel map based on the similarity.

The preprocessor is configured to detect a blood vessel region included in the TOF image, and extract a center line connecting voxels located at a center of the blood vessel from among the voxels in the blood vessel by using a distance between the voxels included in the blood vessel region and a boundary line of the blood vessel and a geodesic distance between the voxels.

The matching unit is configured to match the TOF image with the reference blood vessel image in consideration of center lines included in the TOF image and the reference blood vessel image.

The similarity calculator is configured to calculate a similarity between a blood vessel center line of the TOF image and a blood vessel center line of the reference blood vessel image and a correspondence relationship between the similarities, by calculating a similarity between the point of the TOF image and the point of the reference blood vessel image, and repeatedly calculating the similarity between the points.

A computer program according to an embodiment of the present invention may be stored in a computer-readable storage medium for executing any one of methods of constructing a blood vessel map according to an embodiment of the present invention using a computer.

In addition to this, another method for implementing the present invention, another system, and a computer-readable recording medium for recording a computer program for executing the method are further provided.

Other aspects, features and advantages other than those described above will become apparent from the following drawings, claims, and detailed description of the invention.

Advantageous Effects of Disclosure

According to embodiments of the present invention, an average blood vessel image based on to the age and region of Koreans may be obtained.

Also, according to embodiments of the present invention, a similarity between a blood vessel-related disease and a blood vessel shape can be obtained, and based on this, the vascular disease of the object may be predicted in advance.

BEST MODE

Figure 1:
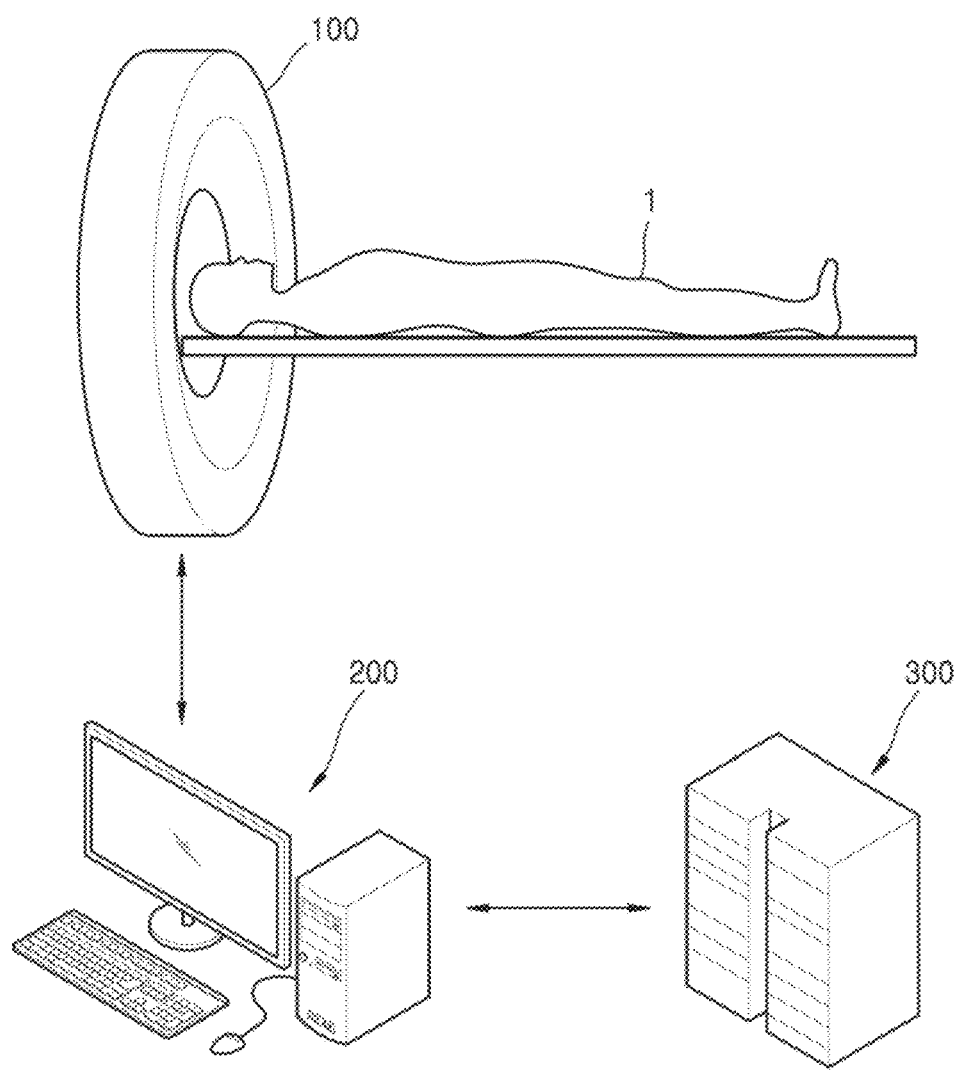
FIG. 1 is a block diagram of a blood vessel map construction system according to embodiments of the present invention.

Hereinafter, example embodiments according to the present invention will be described in detail with reference to the descriptions in the accompanying drawings. In addition, a method of configuring and using an electronic device according to an embodiment of the present invention will be described in detail with reference to the accompanying drawings. The same reference numbers or reference numerals presented in each drawing indicate parts or elements that perform substantially the same functions.

Terms including an ordinal number, such as first, second, etc., may be used to describe various elements, but the elements are not limited by the terms. The terms are used only for the purpose of distinguishing one component from another. For example, without departing from the scope of the present invention, a first element may be referred to as a second element, and similarly, a second element may also be referred to as a first element. The term 'and/or' includes a combination of a plurality of related items or any one of a plurality of related items.

The terms used herein are used to describe the embodiments, and are not intended to limit and/or restrict the present invention. The singular expression includes the plural expression unless the context clearly dictates otherwise. It should be understood that the term 'include' or 'have' in the present application is intended to designate that a feature, number, step, operation, element, part, or combination thereof described in the specification exists, and does not preclude the possibility of the presence or addition of other features or numbers, steps, operations, elements, prats, or combinations thereof.

Throughout the specification, when it is said that a part is connected to another part, this includes not only a case in which it is directly connected, but also a case in which it is electrically connected with another element interposed therebetween. Also, when it is said that a part includes a certain element, this means that other elements may be further included, rather than excluding other components, unless otherwise stated. In addition, terms such as " . . . unit" and "module" described in the specification mean a unit that processes at least one function or operation, which may be implemented as hardware or software, or a combination of hardware and software.

In the present specification, an image may refer to multidimensional data composed of discrete image elements (e.g., pixels in a 2D image and voxels in a 3D image). For example, the image may include a medical image of an object obtained by an X-ray apparatus, a CT apparatus, an MRI apparatus, an ultrasound diagnosis apparatus, and another medical imaging apparatus.

In the present specification, the object may include a human or animal, or a part of a human or animal. For example, the object may include a device or blood vessel such as a liver, heart, uterus, brain, breast, and abdomen. In addition, the object may include a phantom. The phantom refers to a material having a volume very close to the density and effective atomic number of an organism, and may include a spherical phantom having properties similar to that of a body.

In the present specification, a user may be a medical professional, such as a doctor, a nurse, a clinical pathologist, a medical imaging specialist, or a technician repairing a medical device, but is not limited thereto.

In the present specification, time-of-flight (TOF) magnetic resonance angiography (MRA) is an imaging technique that emphasizes blood flow in an object without using a contrast agent, and is widely used to image intracranial cerebral artery blood vessels. Because TOF MRA is obtained by shortening the repetition time, the signal intensity is reduced due to the application of repetitive radiofrequency (RF) pulses for a short time in a stationary tissue. However, because water molecules moving along a blood vessel leave a slice to which the RF pulse is applied, they do not experience repeated RF pulses, so the signal intensity is relatively high. Therefore, there is an advantage in that it is easy to extract a blood vessel based on the signal intensity from an image obtained by using TOF MRA.

FIG. 1 is a block diagram of a blood vessel map construction system according to embodiments of the present invention.

A blood vessel map construction system 10 may include an imaging apparatus 100, a blood vessel map construction apparatus 200, and a blood vessel database 300.

The blood vessel map construction system 10 may transmit a blood vessel image obtained through the imaging apparatus 100 to the blood vessel map construction apparatus 200, and the blood vessel map construction apparatus 200 may analyze the blood vessel image to standardize and normalize the blood vessel image of the object. For example, a standard blood vessel image of a 20-year-old woman and a standard blood vessel image of a 35-year-old man may be set from the blood vessel images of the objects.

Also, the blood vessel map construction apparatus 200 may predict a vascular disease of the object in advance through a reference blood vessel image corresponding to the blood vessel of the object.

The imaging apparatus 100 is a device that outputs an image obtained by measuring an object, and may be an X-ray apparatus, a CT apparatus, an MRI apparatus, an ultrasound diagnosis apparatus, or other medical imaging apparatus. The imaging apparatus 100 may obtain a blood vessel image of all or part of the object. The imaging apparatus 100 may photograph the object and output various image outputs such as a time-of-flight (TOF) image.

The blood vessel map construction apparatus 200 may receive a blood vessel image of an object and construct a blood vessel map by comparing the blood vessel image with the reference blood vessel image. The blood vessel map construction apparatus 200 may calculate a similarity between first point of a reference blood vessel and second point of a received blood vessel image, a correspondence relationship between first point and second point, and the like by using a blood vessel segmentation region and/or a blood vessel center line obtained from the input image. The blood vessel map construction apparatus 200 may update the blood vessel database through the blood vessel image of the object based on the calculated similarity and correspondence relationship with the reference blood vessel. The blood vessel map construction apparatus 200 transmits the blood vessel map information of each object to the blood vessel database stored in the external database 300 so that the blood vessel map in the database 300 is updated. The blood vessel map construction apparatus 200 may convert the processed blood vessel image and similarity information with respect to the blood vessel image into a storage format stored in the blood vessel database. The blood vessel map construction apparatus 200 may be a computing device including one or more processors and a storage medium.

The blood vessel database 300 refers to a database device for reference blood vessels based on measured blood vessel images, similarity information for blood vessel images, and biometric information, and may be connected to the blood vessel map construction apparatus 200 electrically or through a communication network.

Figure 2:
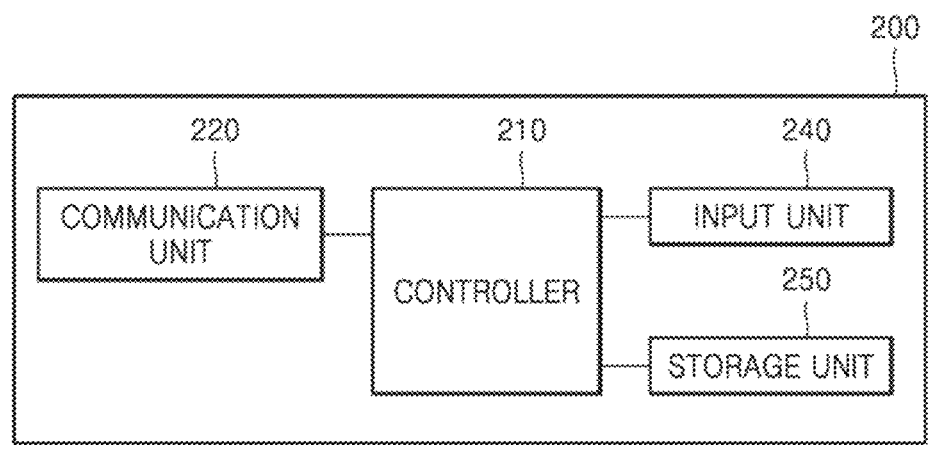
FIG. 2 is a block diagram of an apparatus for constructing a blood vessel map according to embodiments of the present invention.
Figure 3:
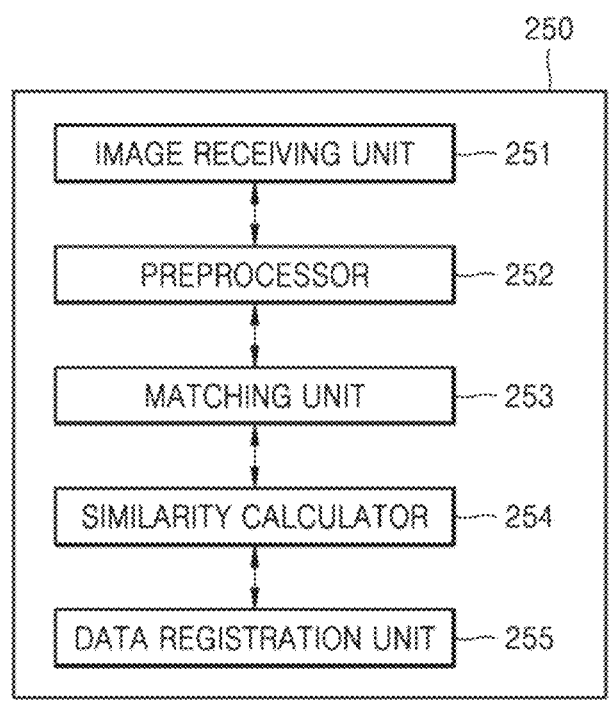
FIG. 3 is a block diagram illustrating a structure of a storage unit.

FIG. 2 is a block diagram of a blood vessel map construction apparatus according to embodiments of the present invention.

A blood vessel map construction apparatus 200 may include a controller 210, a communication unit 220, an input unit 240, and a storage unit 250.

The controller 210 may be implemented with one or more processors, and may be configured to process instructions of a computer program by performing basic arithmetic, logic, and input/output operations. The instructions may be provided to the controller 210 by the storage unit 250 and the communication unit 220. For example, the controller 210 may be configured to execute a received instruction depending on a program code stored in a recording device such as the storage unit 250.

The communication unit 220 may provide a function for communicating with an external device through a network. For example, a request generated by the controller 210 of the blood vessel map construction apparatus 200 based on a program code stored in a recording device such as the storage unit 250 may be transmitted to the external imaging apparatus 100, the database 300, or another user terminal through a network under the control of the communication unit 220. For example, a control signal or command received through the communication unit 220 may be transmitted to the controller 210 or the storage unit 250, and the received image may be stored in the storage unit 250.

The storage unit 250 is a computer-readable recording medium and may include a random access memory (RAM), a read only memory (ROM), and a permanent mass storage device such as a disk drive. In addition, the storage unit 250 may store an operating system and at least one program code. These software components may be loaded from a computer-readable recording medium separate from the storage unit 250 using a drive mechanism. The separate computer-readable recording medium may include a computer-readable recording medium such as a floppy drive, a disk, a tape, a DVD/CD-ROM drive, and a memory card. In another embodiment, the software components may be loaded into the storage unit 250 through the communication unit 220 instead of a computer-readable recording medium. For example, at least one program may be loaded into the storage unit 250 based on a program (e.g., the above-described application) installed by files provided through a network by developers or a file distribution system for distributing installation files of applications.

The input/output unit 240 may receive a user input. For example, the input/output unit 240 may include an operation panel for receiving a user input and a display panel for displaying a screen.

In detail, the input unit may include devices capable of receiving various types of user input, such as a keyboard, a physical button, a touch screen, a camera, or a microphone. In addition, the output unit may include a display panel or a speaker. However, the present invention is not limited thereto, and the input/output unit 240 may include a configuration supporting various input/output.

In order to analyze and process the image of the object to construct a blood vessel map, the blood vessel map construction apparatus 200 may include an image receiving unit 251, a preprocessor 252, a matching unit 253, a similarity calculator 254, and a data registration unit 255.

The image receiver 251 may receive one or more images obtained by photographing the object. The image receiving unit 251 receives a TOF image.

The preprocessor 252 detects a blood vessel region included in the TOF image, and extracts a center line of the blood vessel and features of the center line (diameter length, location, position of branch points, and boundary line information of the blood vessel) from the blood vessel region. The preprocessor 252, in the TOF image, represents a voxel corresponding to a blood vessel as 1, and represents a voxel that is not a blood vessel as 0. The preprocessor 252 extracts centerlines and features of the centerlines of the blood vessel segments included in the TOF image. Distances between voxels in the blood vessel and the border of the blood vessel may be calculated, the voxel having the longest distance from the border of the blood vessel in the cross section of the blood vessel may be extracted, and a set of these voxels may be extracted as a center line. The preprocessor 252 may obtain information about the branch and branch points of the blood vessel distributed in the blood vessel, which are characteristics of the center line of the blood vessel, by extracting the center line of the blood vessel. The preprocessor 252 may additionally obtain which blood vessel is a blood vessel or an anatomical name of the blood vessel by using the obtained information.

The preprocessor 252 may detect the blood vessel region included in the TOF image, extract voxels located at the center of the blood vessel as a center line, from among voxels in the blood vessel by using the distance between the voxels included in the blood vessel region and the boundary line of the blood vessel and the geodesic distance between the voxels, and obtain information on the blood vessel stem and branch points distributed in the blood vessel, which are characteristics of the center line of the blood vessel.

The matching unit 253 matches the TOF image with the reference vessel image by using the vessel centerline of the TOF image and the vessel centerline included in the reference vessel image. The matching unit 253 matches by changing the position and direction so that the distance between the center lines is close. The matching unit 253 searches for a reference blood vessel image corresponding to the TOF image, and matches the TOF image with the reference blood vessel image in consideration of information (position, curvature, etc.) on the branch of the blood vessel and branch points of the blood vessel included in the TOF image and the reference blood vessel image. The matching unit 253 detects a second point of a reference blood vessel image corresponding to information on a branch point of a first point of the TOF image, for example, a position and a curvature, respectively, and aligns the TOF image and the reference blood vessel image by locating the two detected points in proximity.

Figure 8A:
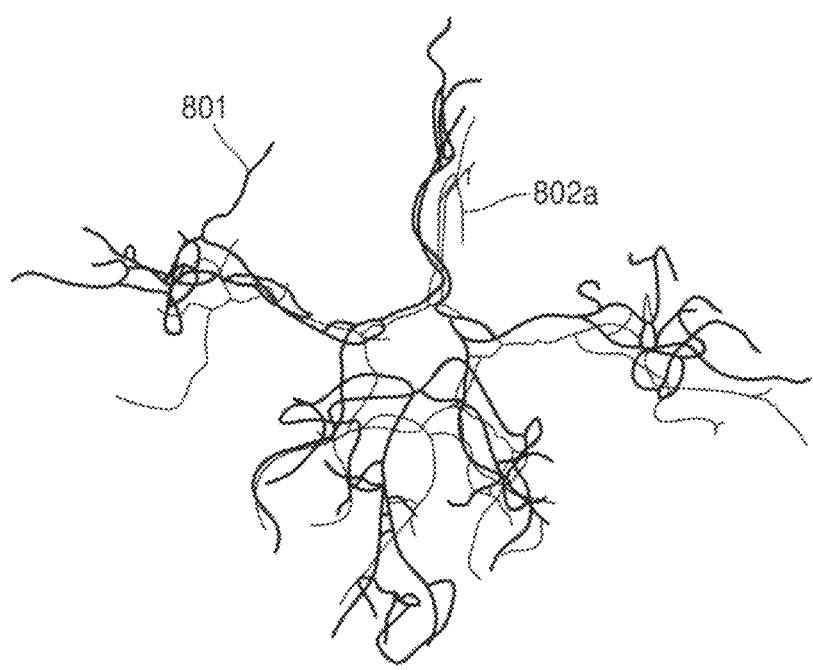
FIG. 8A and FIG. 8B are example views in which a TOF image and a reference blood vessel image are matched.
Figure 8B:
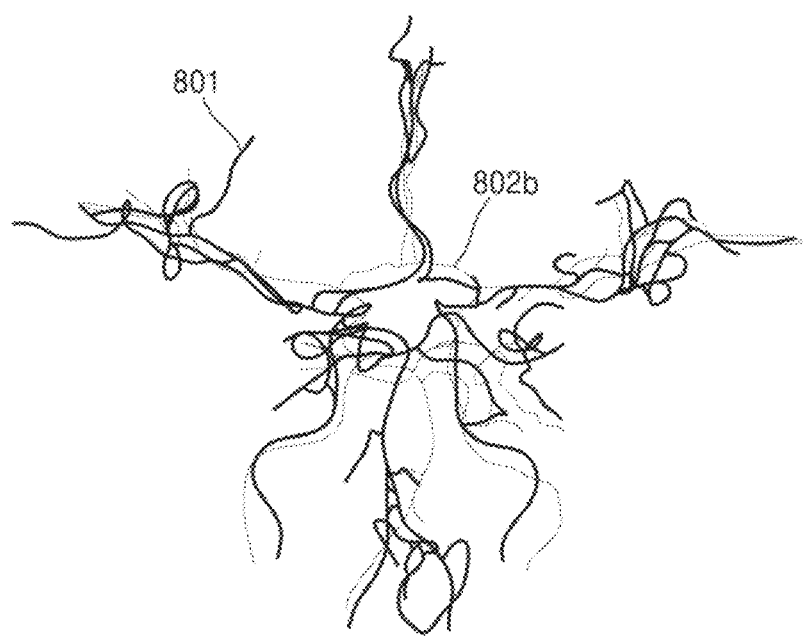

The matching unit 253 may search for a reference vessel image by using the vessel branch information, boundary line information, the diameter of the vessel, the center line, and the like for the TOF image obtained through the preprocessor 252. The matching unit 253 aligns points corresponding to the TOF image and the reference blood vessel image in a short distance by using the center line and characteristics of the center line of the blood vessel. In another embodiment, the matching unit 253 may align points corresponding to the TOF image and the reference blood vessel image in a short distance by using shape information (position, curvature, etc.) of the branch points of the blood vessel. As shown in FIG. 8A and FIG. 8B, before alignment, the reference vessel image 801 and the vessel 802a of the TOF image are arranged not to be aligned, but after alignment, the position, direction, ratio, etc. of the TOF image may be modified so as to be positioned close to the reference blood vessel image 801 and expressed as 802b.

The similarity calculator 254 may calculate a similarity between the point of the TOE image and the point of the reference blood vessel image. The similarity calculator 254 may calculate the similarity by comparing feature values between a point corresponding to a blood vessel in the TOF image and a point corresponding to a blood vessel in the reference blood vessel image. The similarity calculator 254 calculates a similarity (a distance difference value between the points, a curvature difference value, a blood vessel diameter difference value, a vector value difference value, a branch information difference value, etc.) between the first point of the TOF image and the second point of the reference blood vessel image matched to the TOF image. The similarity between the first point and the second point may be increased as the respective values are smaller.

In another embodiment, the similarity calculator 254 selects an arbitrary point in the TOF image, selects one or more candidate group points to be matched with the point from the reference blood vessel image using the matched result, and calculates similarity by comparing points of the TOF image with points of the candidate group of the reference blood vessel image, respectively. The candidate group points refer to points of the reference blood vessel image located close to the point of the TOF image. The candidate group points refer to all or some of the points of the reference blood vessel image located within a preset distance value from the point of the TOE image. It is determined that a pair of points having the smallest feature value difference between the points corresponds.

The similarity calculator 254, while repeating the process of calculating the similarity by comparing the points of the TOF image with the points of the reference blood vessel image, calculates similarities between the vessel centerline of the TOF image and the vessel centerline of the reference blood vessel image, and determines whether the calculated similarities have the same correspondence relationship. The correspondence relationship between similarities is calculated between two or more points. The similarity calculator 254 calculates a probability that may be corresponded in pairs in consideration of similarities between two points of a TOF image and two points of a reference blood vessel image and the correspondence relationship between similarities, and designates a correspondence relationship between the blood vessel center line and the blood vessel center line of the reference blood vessel image by using the probability that may be corresponded in pairs. The similarity calculator 254 may calculate similarities between points corresponding to blood vessels in the TOF image and points corresponding to blood vessels in the reference blood vessel image, and calculate the correspondence relationship between the similarities. The similarity calculator 254 may align the calculated correspondence relationship from the viewpoint of the blood vessel stem topology of the TOF image, and regenerate the correspondence relationship of the similarities based on the aligned information. The similarity calculating unit 254 may align the blood vessel stems based on the topological structure, and regenerate the correspondence relationship between the similarities based on the aligned information.

The similarity information calculated by the similarity calculator 254 is registered as information on the object and the TOF image.

The data registration unit 255 registers the TOF image in the blood vessel map database by synthesizing the TOF image and similarity information with respect to the TOF image.

The data registration unit 255 determines an object group based on biometric information of the objects, and registers the TOF image of the object and similarity information on the TOF image by linking the TOF image and the similarity information with the object group. For example, when the similarity information for the TOF image is detected by analyzing the first TOF image of a woman in her twenties, the similarity information on the TOF image obtained through comparison with the reference blood vessel image belonging to a woman in her twenties is limited to the subject and registered.

The data registration unit 255 may diagnose a vascular disease of the object, a possibility of future vascular disease, a type of a vascular disease to occur in the future, and the like through the reference blood vessel image found in correspondence with the TOF image of the object. In addition, the data registration unit 255 may determine the possibility of development of diseases previously diagnosed based on periodically photographed TOF images of the object. The data registration unit 255 may transmit diagnostic information and information such as development potential to a terminal of the object or a terminal of a manager of the object. In this case, the manager of the object may be registered with approval from the object and a medical institution.

As described above, according to embodiments of the present invention, a standard blood vessel image may be produced by statistically processing the center line and features of the center line of the blood vessel. According to embodiments of the present invention, a standard blood vessel image based on each condition of users may be produced by statistically processing the position value of the blood vessel stems, the center lines, and the feature values of the center lines. A standard shape of a blood vessel that meets various conditions may be registered, such as a standard blood vessel for a woman in her 20s, a standard blood vessel for a man in her 30s, and a standard blood vessel for a man with cerebral infarction.

Figure 4:
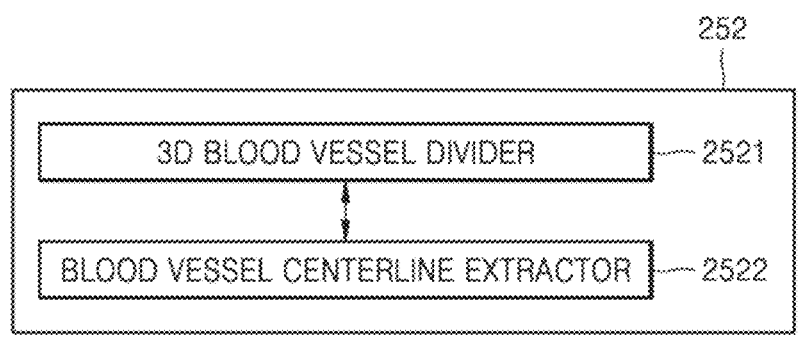
FIG. 4 is a block diagram illustrating the structure of a preprocessor.

Next, a structure of the preprocessor 252 will be described in detail with reference to FIG. 4.

The preprocessor 252 may include a 3D blood vessel divider 2521 and a blood vessel centerline extractor 2522.

In order to evenly distribute voxel values included in the TOF image, the 3D blood vessel divider 2521 may convert voxel values of the TOF image by using histogram smoothing. The 3D blood vessel divider 2521 may set a reference value by multiplying an average value of voxel values included in the TOF image by an arbitrary integer in order to extract the blood vessel region after the histogram smoothing, and may detect the blood vessel region by setting voxels greater than the reference value to 1 and voxels less than the reference value to 0.

In order to correct the blood vessel region, when the number of voxels constituting one component is extremely small, for example, when less than 0.01% of the total number of voxels, the 3D blood vessel divider 2521 regards voxels divided into corresponding blood vessel branches as noise and removes the noise, wherein the one component refers to a portion in which portions detected as one blood vessel region are adjacently connected.

The blood vessel center line extractor 2522 may extract the center line of the blood vessel based on distances of voxels inside the blood vessel from the edge line of the blood vessel. In detail, the blood vessel centerline extractor 2522 obtains distances from the boundary line of the vessel to voxels inside the vessel, and extracts the voxel having the longest distance to the boundary line of the vessel from among voxels existing in an arbitrary cross-section of the vessel. A voxel having the longest distance to the boundary line may be designated as source points. The blood vessel centerline extractor 2522 obtains geodesic distances between voxels constituting a blood vessel from source points, and designates a voxel located farthest from the source point as a start point based on the geodesic distances. The blood vessel centerline extractor 2522 extracts a centerline connecting the voxels extracted through this process. The blood vessel centerline extractor 2522 sets the shortest path connecting between the source point and the start point as a centerline. In this case, a boundary line located at the closest distance to each voxel may be selected as the boundary line of the blood vessel. The blood vessel centerline extractor 2522 extracts a centerline by designating an arbitrary voxel included in the centerline as a second source point. In this case, the above process (the process of designating the source point, designating the starting point, and extracting the center line) is repeated until the length of the center line becomes smaller than the diameter of the blood vessel.

The blood vessel centerline extractor 2522 may obtain information on the branch points of the blood vessel while extracting the centerline of the blood vessel. The blood vessel centerline extractor 2522 may calculate a geodesic distance from any first voxel included in the centerline to another voxel in the centerline, and may set a voxel having the longest geodesic distance as a starting point of a next branch point. The blood vessel centerline extractor 2522 may detect branch points distributed in the blood vessel using the geodesic distance.

Through these processes, it is possible to obtain information on the branch of the blood vessel distributed in the blood vessel, information on the boundary line, the diameter of the blood vessel, and the like.

MODE OF DISCLOSURE

Figure 5:
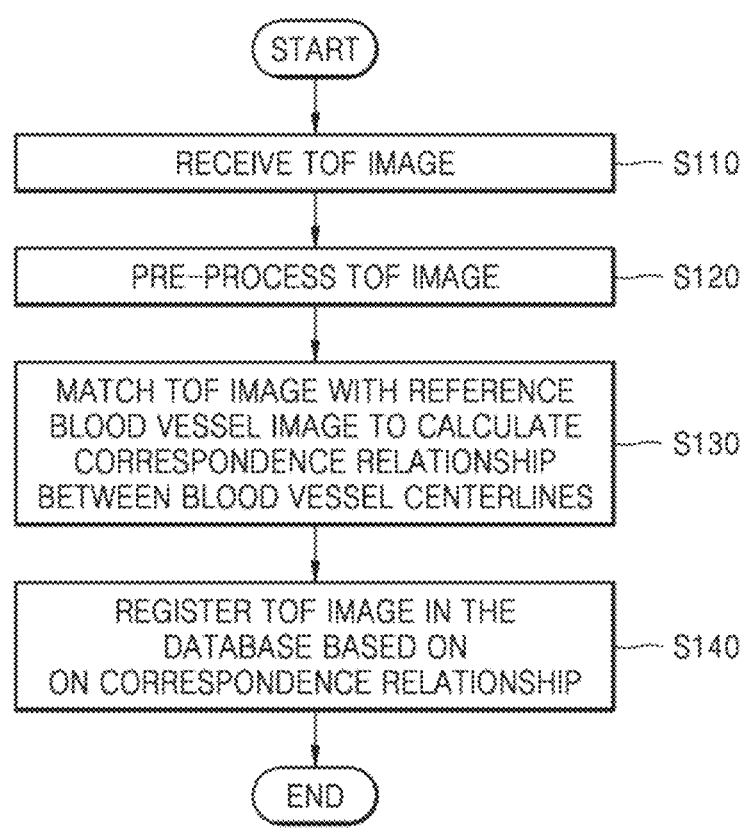
FIGS. 5 to 7 are flowcharts of a method of constructing a blood vessel map according to embodiments of the present invention.
Figure 6:
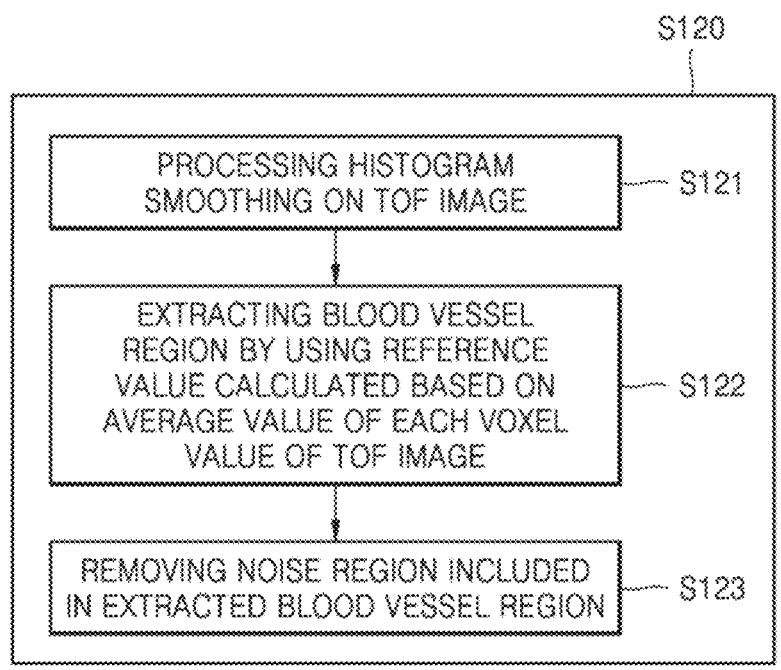
Figure 7:
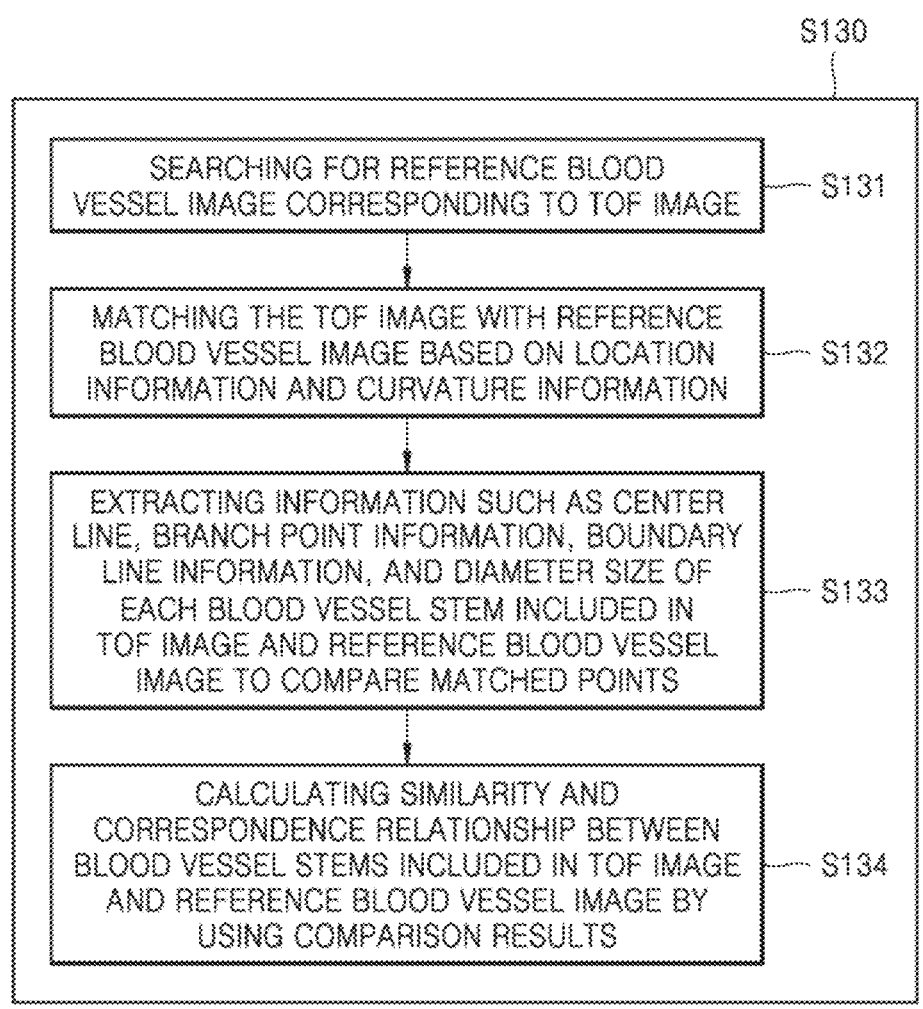

FIGS. 5 to 7 are flowcharts of a method of constructing a blood vessel map according to embodiments of the present invention.

In operation S110, the blood vessel map construction apparatus 200 receives a TOF image of the blood vessel of the object from the imaging apparatus 100.

In operation S120, the blood vessel map construction apparatus 200 pre-processes the TOF image. Through the pre-processing process, the blood vessel region included in the TOF image may be extracted, and shape information (position, curvature, etc.) of blood vessel stems (branches) included in the blood vessel region and labeling information on the blood vessel stems may be generated.

In operation S130, the blood vessel map construction apparatus 200 matches the TOF image with the reference blood vessel image to calculate a correspondence relationship between blood vessel centerlines. The blood vessel map construction apparatus 200 searches for a reference blood vessel image based on the shape information on the blood vessel stems for the TOF image, the labeling information on the blood vessel stems, and the like, and matches the TOF image with the reference vessel image by modifying the arrangement position and direction of the TOF image in consideration of the positions of the vessel stems and branch points of the reference vessel image.

In a state in which the TOF image is matched with the reference blood vessel image, a similarity between adjacent blood vessel stems and branch points may be calculated. In this case, similarities between corresponding blood vessel stems in the TOF image and the reference blood vessel image and a correspondence relationship between the similarities are calculated. Whether or not the similarity (distance difference value, curvature difference value, blood vessel diameter difference value, etc.) between a plurality of points belonging to the blood vessel stem has a similar direction or an opposite direction may be calculated as the correspondence relationship.

In operation S140, the vessel map construction apparatus 200 registers the TOF image in the database based on the similarity between the vessel stems and the similarity between the vessel branch points calculated by using the matched TOF image and the reference vessel image.

As shown in FIG. 6, the pre-processing of the TOF image may include an operation S121 of processing a histogram smoothing on the TOF image, an operation S122 of extracting the blood vessel region by using a reference value calculated based on an average value of each voxel value of the TOF image, and an operation S123 of removing a noise region included in the extracted blood vessel region.

The blood vessel map construction apparatus 200 may uniformly distribute voxel values included in the TOF image by converting voxel values of the TOF image using histogram smoothing. In detail, the blood vessel map construction apparatus 200 may derive a new voxel value by applying the voxel value of the TOF image to a preset equation, and may smooth by replacing an existing voxel value with the new voxel value. The blood vessel map construction apparatus 200 may detect or extract the blood vessel region, by multiplying the average value of voxel values included in the TOF image by an arbitrary integer to set a reference value and setting voxels greater than the reference value as 1 and voxels less than the reference value as 0.

When the number of voxels included in a partial region of one blood vessel region is extremely small, for example, when the number of voxels is 0.01% or less of the total number of voxels, the blood vessel map construction apparatus 200 may more clearly correct the blood vessel region by removing the voxels divided into the corresponding blood vessel branch as noise.

The blood vessel map construction apparatus 200 may extract the center line of the blood vessel based on distances of voxels inside the blood vessel from the edge line of the blood vessel. In detail, the blood vessel map construction apparatus 200 obtains distances from the boundary line of the blood vessel to voxels inside the blood vessel, and extracts the voxel having the longest distance to the boundary line of the blood vessel among voxels existing in an arbitrary cross-section of the blood vessel. The blood vessel map construction apparatus 200 extracts a center line connecting the voxels extracted through this process. In this case, the boundary line of the blood vessel may be selected as the boundary line located at the closest distance to each voxel.

The blood vessel map construction apparatus 200 may obtain branch information of blood vessels while extracting the center line of the blood vessels. The blood vessel map construction apparatus 200 may calculate a geodesic distance from any first voxel included in the center line to other voxels in the center line, and may set a voxel having the longest geodesic distance as a starting point of a next branch. The blood vessel map construction apparatus 200 may detect branches distributed in the blood vessel by using the geodesic distance. The blood vessel map construction apparatus 200 may extract a blood vessel centerline using the geodesic distance and, at the same time, specify a blood vessel stem, and may also specify a blood vessel branch point based on the blood vessel stem.

As shown in FIG. 7, the operation S130 may include an operation S131 of searching for a reference blood vessel image corresponding to the TOF image, an operation 132 of matching the TOF image with the reference blood vessel image based on location information and curvature information, an operation S133 of extracting information such as center line, branch point information, boundary line information, and diameter size of each blood vessel stem included in the TOF image and the reference blood vessel image to compare the matched points, and operation S134 of calculating a similarity and a correspondence relationship between the blood vessel stems included in the TOF image and the reference blood vessel image by using the comparison results.

In operation S132, the vessel map construction apparatus 200 searches for the reference vessel image corresponding to the TOF image, and matches the TOF image with the reference blood vessel image in consideration of branch of blood vessel, center line of the blood vessel, and characteristics of the center line included in the TOF image and the reference blood vessel image. The blood vessel map construction apparatus 200 matches the blood vessel included in the TOF image with the blood vessel included in the reference blood vessel image to be located closest to each other. In this case, the distances between the center points of the blood vessel of the TOF image and the center points of the blood vessel of the reference blood vessel image are respectively calculated. The vessel map construction apparatus 200 matches the TOF image with the reference vessel image by using the vessel centerline of the TOF image and the vessel centerline included in the reference vessel image. The blood vessel map construction apparatus 200 matches by converting the position and direction so that the distance between the center lines is close.

In operation S133, the blood vessel map construction apparatus 200 may calculate similarities between points of the TOF image and blood vessel stems (or center lines) of the reference blood vessel image, and may calculate a correspondence relationship. The blood vessel map construction apparatus 200 may detect a point 2-1 and a point 2-2 included in the blood vessel stem corresponding to the blood vessel stem of a reference blood vessel image, which are matched with the point 1-1 and the point 1-2 included in one vascular stem of TOF image, may calculate a first similarity between the point 1-1 and the point 2-1 and a second similarity between the point 1-2 and the point 2-2, and may calculate the correspondence relationship between the first similarity and the second similarity. The blood vessel map construction apparatus 200 may calculate a similarity between the point of the TOF image and the point of the reference blood vessel image. The blood vessel map construction apparatus 200 may calculate similarity by comparing feature values between a point corresponding to a blood vessel in the TOE image and a point corresponding to a blood vessel in the reference blood vessel image. The blood vessel map construction apparatus 200 calculates a similarity (a distance difference value between the points, a curvature difference value, a blood vessel diameter difference value, a vector value difference value, a branch information difference value, etc.) between the first point of the TOF image and the second point of the reference blood vessel image matched with the TOF image. The similarity between the first point and the second point may be increased as the respective values are smaller.

In another embodiment, the blood vessel map construction apparatus 200 selects any one point in the TOF image, selects one or more candidate group points to correspond to the point from the reference blood vessel image by using the matched result, and then calculates similarity by comparing points of the TOF image with candidate group points of the reference blood vessel image, respectively. The candidate group points refer to points of the reference blood vessel image located close to the point of the TOF image. The candidate group points refer to all or some of the points of the reference blood vessel image located within a preset distance value from the point of the TOF image. It is determined that a pair of points having the smallest feature value difference between the points corresponds.

FIG. 9 is an example diagram illustrating labeled states of vascular regions and vascular stems extracted by a preprocessor.

Figure 9A:
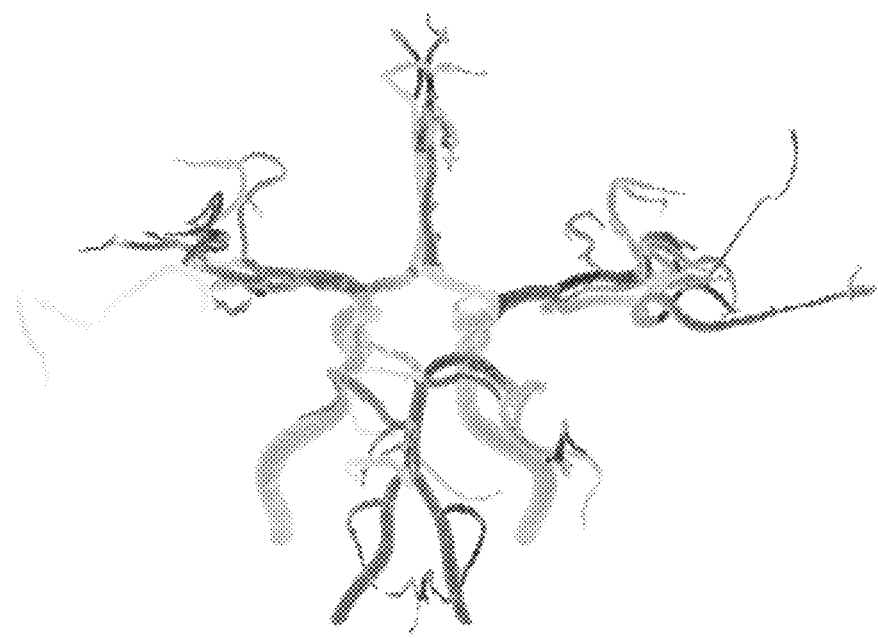
FIGS. 9A and 9B are example views illustrating blood vessel regions and blood vessel centerlines extracted by a preprocessor.

As shown in FIG. 9A, the blood vessel map construction apparatus 200 may represent blood vessel stems in different colors, and may register separate location information, curvature information, branch point information, blood vessel diameter information, and the like for the blood vessel stems represented in different colors.

Figure 9B:
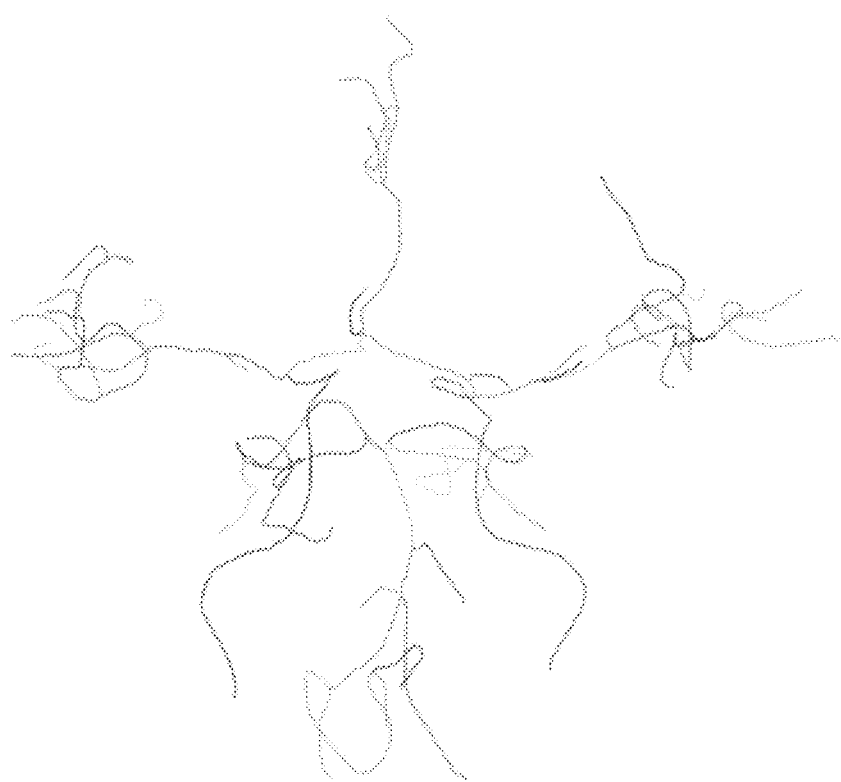

As shown in FIG. 9B, the blood vessel map construction apparatus 200 may extract centerlines by using distances to voxels in the blood vessel, geodesic distances between the voxels, and the like. The voxels in the blood vessel may be randomly selected.

The device described above may be implemented as a hardware component, a software component, and/or a combination of the hardware component and the software component. For example, the apparatus and components described in the embodiments may be implemented using one or more general-purpose computers or special-purpose computers, for example, such as a processor, controller, arithmetic logic unit (ALU), digital signal processor, microcomputer, field programmable gate array (FPGA), programmable logic unit (PLU), microprocessor, or any other device capable of executing and responding to instructions. The processing device may also access, store, manipulate, process, and generate data in response to execution of the software. The processing device may also access, store, manipulate, process, and generate data in response to execution of the software. For ease of understanding, it may be described that a single processing device is used as a single processing element, but a person of ordinary skill in the art will recognize that a processing device may include a plurality of processing elements and/or a plurality of types of processing elements. For example, the processing device may include a plurality of processors or one processor and one controller. Other processing configurations are also possible, such as parallel processors.

Software may include a computer program, code, instructions, or a combination of one or more of these, and may configure the processing device to operate as desired, or independently or collectively, instruct the processing device. The software and/or data may be permanently or temporarily embodied in any kind of machine, component, physical device, virtual equipment, computer storage medium or device, or transmitted signal wave, to be interpreted by or to provide instructions or data to the processing device. The software may be distributed over a networked computer system, and stored or executed in the distributed manner. The software and data may be stored in one or more computer-readable recording media.

The method according to the embodiment may be implemented in the form of program instructions that may be executed through various computer means and recorded in a computer-readable medium. The computer-readable medium may include program instructions, data files, data structures, etc. alone or in combination. The program instructions recorded on the medium may be specially designed and configured for the embodiment, or may be known and available to those skilled in the art of computer software. Examples of the computer-readable recording medium include magnetic media such as hard disks, floppy disks and magnetic tapes, optical media such as CD-ROMs and DVDs, and magneto-optical media such as floptical disks, and hardware devices specially configured to store and execute program instructions such as a ROM, a RAM, a flash memory, and the like. Examples of program instructions include not only machine language codes such as those generated by a compiler, but also high-level language codes that may be executed by a computer using an interpreter or the like. The hardware devices described above may be configured to operate as one or more software modules to perform the operations of the embodiments, and vice versa.

As described above, although the embodiments have been described with reference to the limited embodiments and drawings, various modifications and variations are possible from the above description by those skilled in the art. For example, even if the described techniques are performed in an order different from the described method, and/or the components of the described systems, structures, apparatuses, circuits, etc., are coupled or combined in a different form than the described methods, or replaced or substituted by other components or equivalents, appropriate results may be obtained.

Therefore, other implementations, other embodiments, and equivalents to the claims are also within the scope of the following claims.

The invention claimed is:

1. A method of constructing a blood vessel map, the method
receiving, by a blood vessel map construction apparatus, a TOF image of the object;
extracting, by the blood vessel map constriction apparatus, a blood vessel stem, a center line of a blood vessel, and features of the center line included in the TOF image, and detecting branch points of the blood vessel based on the extracted blood vessel stem, center line of the blood vessel, and features of the center line;
searching, by the blood vessel map construction apparatus, a reference blood vessel image corresponding to the TOF image in consideration of location information or curvature information of the branch points;
calculating a similarity between the TOF image and the reference blood vessel image; and
registering the TOF image in the blood vessel map based on the similarity.

2. The method of claim 1, wherein the extracting of the blood vessel stein, the center line of the blood vessel, and the features of the center line includes detecting a blood vessel region included in the TOF image, extracting a center line connecting voxels located at the center of the blood vessel from among voxels in the blood vessel by using a distance between voxels included in the blood vessel region and a boundary line of the blood vessel and a geodesic distance between the voxels, and obtaining information about the blood vessel stems and the branch points distributed in the blood vessels.

3. The method of claim 2, wherein alter the searching of the reference blood vessel image, the TOF image is matched with the reference blood vessel image in consideration of centerlines of a blood vessel included in the TOF image and the reference blood vessel image.

4. The method of claim 3, wherein the calculating of the similarity includes calculating a similarity between the blood vessel center line of the TOF image and a blood vessel center line of the reference blood vessel image and a correspondence relationship between the similarities, by calculating a similarity between the point of the TOF image and the point of the reference blood vessel image, and repeatedly calculating the similarity between the points.

5. A computer program stored in a computer-readable storage medium for executing the method of claim 1 using a computer.

6. A blood vessel map construction apparatus, comprising:
an image input unit configure to receive a TOF image of the object;
a preprocessor configured to extract a blood vessel stem, a center line of a blood vessel, and features of the center line included in the TOF image, and detect branch points of the blood vessel based on the extracted blood vessel stem, center line of the blood vessel, and features of the center line;
a matching unit configure to search for a reference blood vessel image corresponding to the TOE image in consideration of location information or curvature information of branch points;
a similarity calculator configured to calculate a similarity between the TOF image and the reference blood vessel image; and
a data registration unit configured to register the TOF image in a blood vessel map based on the similarity.

7. The blood vessel map construction apparatus of claim 6, wherein the preprocessor is configured to detect a blood vessel region included in the TOF image, and extract a center line connecting voxels located at a center of the blood vessel from among the voxels in the blood vessel by using a distance between the voxels included in the blood vessel region and a boundary line of the blood vessel and a geodesic distance between the voxels.

8. The blood vessel map construction apparatus of claim 7, wherein the matching unit is configured to match the TOF image with the reference blood vessel image in consideration of center lines included in the TOF image and the reference blood vessel image.

9. The blood vessel map construction apparatus of claim 8, wherein the similarity calculator is configured to calculate a similarity between a blood vessel center line of the TOF image and a blood vessel center line of the reference blood vessel image acid a correspondence relationship between the similarities, by calculating a similarity between the point of the TOF image and the point of the reference blood vessel image, and repeatedly calculating the similarity between the points.

\* \* \* \* \*